(12) United States Patent
Kling et al.

(10) Patent No.: US 7,881,762 B2
(45) Date of Patent: Feb. 1, 2011

(54) CLIP-STYLE MEDICAL SENSOR AND TECHNIQUE FOR USING THE SAME

(75) Inventors: Carl Kling, San Ramon, CA (US); Phillip S. Palmer, San Leandro, CA (US); Robert W. Flagler, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1079 days.

(21) Appl. No.: 11/239,809

(22) Filed: Sep. 30, 2005

(65) Prior Publication Data

US 2007/0078315 A1     Apr. 5, 2007

(51) Int. Cl.
*A61B 5/1455*    (2006.01)

(52) U.S. Cl. ..................... 600/344; 600/323

(58) Field of Classification Search ............... 600/323, 600/344
See application file for complete search history.

(56) References Cited

U.S. PATENT DOCUMENTS

| | | | |
|---|---|---|---|
| 3,403,555 A | 10/1968 | Versaci et al. |
| 3,536,545 A | 10/1970 | Traynor et al. |
| D222,454 S  | 10/1971 | Beeber |
| 3,721,813 A | 3/1973  | Condon et al. |
| 4,098,772 A | 7/1978  | Bonk et al. |
| D250,275 S  | 11/1978 | Bond |
| D251,387 S  | 3/1979  | Ramsay et al. |
| D262,488 S  | 12/1981 | Rossman et al. |
| 4,321,930 A | 3/1982  | Jobsis et al. |
| 4,334,544 A | 6/1982  | Hill et al. |
| 4,350,165 A | 9/1982  | Striese |
| 4,353,372 A | 10/1982 | Ayer |
| 4,380,240 A | 4/1983  | Jobsis et al. |
| 4,406,289 A | 9/1983  | Wesseling et al. |
| 4,510,551 A | 4/1985  | Brainard, II |
| 4,510,938 A | 4/1985  | Jobsis et al. |
| 4,586,513 A | 5/1986  | Hamaguri |
| 4,603,700 A | 8/1986  | Nichols et al. |
| 4,621,643 A | 11/1986 | New, Jr. et al. |
| 4,653,498 A | 3/1987  | New, Jr. et al. |

(Continued)

FOREIGN PATENT DOCUMENTS

DE           3405444        8/1985

(Continued)

OTHER PUBLICATIONS

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp:192-195 (1990).

(Continued)

*Primary Examiner*—Eric F Winakur
(74) *Attorney, Agent, or Firm*—Fletcher Yoder

(57) ABSTRACT

A clip-style sensor is provided that includes a sliding clip, such as a flat spring that slides along the sensor to provide a closing force for the sensor. When the sliding clip is engaged, the sensor is secured to the patient. The sensor may be placed on a patient's finger, toe, ear, and so forth to obtain pulse oximetry or other spectrophotometric measurements.

25 Claims, 4 Drawing Sheets

U.S. PATENT DOCUMENTS

| | | | |
|---|---|---|---|
| 4,677,528 A | 6/1987 | Miniet | |
| 4,685,464 A | 8/1987 | Goldberger et al. | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,722,120 A | 2/1988 | Lu | |
| 4,726,382 A | 2/1988 | Boehmer et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,783,815 A | 11/1988 | Buttner | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hausmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE033,643 E | 7/1991 | Isaacson et al. | |
| 5,028,787 A | 7/1991 | Rosenthal et al. | |
| 5,035,243 A | 7/1991 | Muz | |
| 5,040,539 A | 8/1991 | Schmitt et al. | |
| 5,041,187 A | 8/1991 | Hink et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,086,229 A | 2/1992 | Rosenthal et al. | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H001039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| D326,715 S | 6/1992 | Schmidt | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,207 A | 6/1993 | Rosenthal | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Freidman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,267,566 A | 12/1993 | Choucair et al. | |
| 5,273,036 A | 12/1993 | Kronberg et al. | |
| 5,275,159 A | 1/1994 | Griebel | |
| 5,278,627 A | 1/1994 | Aoyagi et al. | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Freidman et al. | |
| 5,311,865 A | 5/1994 | Mayeux | |
| 5,313,940 A | 5/1994 | Fuse et al. | |
| 5,323,776 A * | 6/1994 | Blakeley et al. | 600/324 |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |

| | | | | | |
|---|---|---|---|---|---|
| 5,343,869 A | 9/1994 | Pross et al. | 5,558,096 A | 9/1996 | Palatnik |
| 5,348,003 A | 9/1994 | Caro | 5,560,355 A | 10/1996 | Merchant et al. |
| 5,348,004 A | 9/1994 | Hollub et al. | 5,564,417 A | 10/1996 | Chance |
| 5,348,005 A | 9/1994 | Merrick et al. | 5,575,284 A | 11/1996 | Athan et al. |
| 5,349,519 A | 9/1994 | Kaestle | 5,575,285 A | 11/1996 | Takanashi et al. |
| 5,349,952 A | 9/1994 | McCarthy et al. | 5,577,500 A | 11/1996 | Potratz |
| 5,349,953 A | 9/1994 | McCarthy et al. | 5,582,169 A | 12/1996 | Oda et al. |
| 5,351,685 A | 10/1994 | Potratz | 5,584,296 A | 12/1996 | Cui et al. |
| 5,353,799 A | 10/1994 | Chance | 5,588,425 A | 12/1996 | Sackner et al. |
| 5,355,880 A | 10/1994 | Thomas et al. | 5,588,427 A | 12/1996 | Tien |
| 5,355,882 A | 10/1994 | Ukawa et al. | 5,590,652 A | 1/1997 | Inai |
| 5,361,758 A | 11/1994 | Hall et al. | 5,595,176 A | 1/1997 | Yamaura |
| 5,365,066 A | 11/1994 | Krueger, Jr. et al. | 5,596,986 A | 1/1997 | Goldfarb |
| 5,368,025 A | 11/1994 | Young et al. | 5,611,337 A | 3/1997 | Bukta |
| 5,368,026 A | 11/1994 | Swedlow et al. | 5,617,852 A | 4/1997 | MacGregor |
| 5,368,224 A | 11/1994 | Richardson et al. | 5,619,992 A | 4/1997 | Guthrie et al. |
| 5,372,136 A | 12/1994 | Steuer et al. | 5,626,140 A | 5/1997 | Feldman et al. |
| 5,377,675 A | 1/1995 | Ruskewicz et al. | 5,630,413 A | 5/1997 | Thomas et al. |
| 5,385,143 A | 1/1995 | Aoyagi | 5,632,272 A | 5/1997 | Diab et al. |
| 5,387,122 A | 2/1995 | Goldberger et al. | 5,632,273 A | 5/1997 | Suzuki |
| 5,390,670 A | 2/1995 | Centa et al. | 5,634,459 A | 6/1997 | Gardosi |
| 5,392,777 A | 2/1995 | Swedlow et al. | 5,638,593 A | 6/1997 | Gerhardt et al. |
| 5,398,680 A | 3/1995 | Polson et al. | 5,638,816 A | 6/1997 | Kiani-Azarbayjany et al. |
| 5,402,777 A | 4/1995 | Warring et al. | 5,638,818 A | 6/1997 | Diab et al. |
| 5,402,779 A | 4/1995 | Chen et al. | 5,645,060 A | 7/1997 | Yorkey et al. |
| 5,411,023 A | 5/1995 | Morris, Sr. et al. | 5,645,440 A | 7/1997 | Tobler et al. |
| 5,411,024 A | 5/1995 | Thomas et al. | 5,660,567 A | 8/1997 | Nierlich et al. |
| 5,413,099 A | 5/1995 | Schmidt et al. | 5,662,105 A | 9/1997 | Tien |
| 5,413,100 A | 5/1995 | Barthelemy et al. | 5,662,106 A | 9/1997 | Swedlow et al. |
| 5,413,101 A | 5/1995 | Sugiura | 5,664,270 A | 9/1997 | Bell et al. |
| 5,413,102 A | 5/1995 | Schmidt et al. | 5,666,952 A | 9/1997 | Fuse et al. |
| 5,417,207 A | 5/1995 | Young et al. | 5,671,529 A | 9/1997 | Nelson |
| 5,421,329 A | 6/1995 | Casciani et al. | 5,673,692 A | 10/1997 | Schulze et al. |
| 5,425,360 A | 6/1995 | Nelson | 5,673,693 A | 10/1997 | Solenberger |
| 5,425,362 A | 6/1995 | Siker et al. | 5,676,139 A | 10/1997 | Goldberger et al. |
| 5,427,093 A | 6/1995 | Ogawa et al. | 5,676,141 A | 10/1997 | Hollub |
| 5,429,128 A | 7/1995 | Cadell et al. | 5,678,544 A | 10/1997 | DeLonzor et al. |
| 5,429,129 A | 7/1995 | Lovejoy et al. | 5,680,857 A | 10/1997 | Pelikan et al. |
| 5,431,159 A | 7/1995 | Baker et al. | 5,685,299 A | 11/1997 | Diab et al. |
| 5,431,170 A | 7/1995 | Mathews | 5,685,301 A | 11/1997 | Klomhaus |
| 5,437,275 A | 8/1995 | Amundsen et al. | 5,687,719 A | 11/1997 | Sato et al. |
| 5,438,986 A | 8/1995 | Disch et al. | 5,687,722 A | 11/1997 | Tien et al. |
| 5,448,991 A | 9/1995 | Polson et al. | 5,692,503 A | 12/1997 | Kuenstner |
| 5,452,717 A | 9/1995 | Branigan et al. | 5,692,505 A | 12/1997 | Fouts |
| 5,465,714 A | 11/1995 | Scheuing | 5,709,205 A | 1/1998 | Bukta |
| 5,469,845 A | 11/1995 | DeLonzor et al. | 5,713,355 A | 2/1998 | Richardson et al. |
| RE035,122 E | 12/1995 | Corenman et al. | 5,724,967 A | 3/1998 | Venkatachalam |
| 5,482,034 A | 1/1996 | Lewis et al. | 5,727,547 A | 3/1998 | Levinson et al. |
| 5,482,036 A | 1/1996 | Diab et al. | 5,730,124 A | 3/1998 | Yamauchi |
| 5,485,847 A | 1/1996 | Baker, Jr. | 5,731,582 A | 3/1998 | West |
| 5,490,505 A | 2/1996 | Diab et al. | D393,830 S | 4/1998 | Tobler et al. |
| 5,490,523 A | 2/1996 | Isaacson et al. | 5,743,260 A | 4/1998 | Chung et al. |
| 5,491,299 A | 2/1996 | Naylor et al. | 5,743,262 A | 4/1998 | Lepper, Jr. et al. |
| 5,494,032 A | 2/1996 | Robinson et al. | 5,743,263 A | 4/1998 | Baker, Jr. |
| 5,494,043 A | 2/1996 | O'Sullivan et al. | 5,746,206 A | 5/1998 | Mannheimer |
| 5,497,771 A | 3/1996 | Rosenheimer | 5,746,697 A | 5/1998 | Swedlow et al. |
| 5,499,627 A | 3/1996 | Steuer et al. | 5,752,914 A | 5/1998 | DeLonzor et al. |
| 5,503,148 A | 4/1996 | Pologe et al. | 5,755,226 A | 5/1998 | Carim et al. |
| 5,505,199 A | 4/1996 | Kim | 5,758,644 A | 6/1998 | Diab et al. |
| 5,507,286 A | 4/1996 | Solenberger | 5,760,910 A | 6/1998 | Lepper, Jr. et al. |
| 5,511,546 A | 4/1996 | Hon | 5,766,125 A | 6/1998 | Aoyagi et al. |
| 5,517,988 A | 5/1996 | Gerhard | 5,766,127 A | 6/1998 | Pologe et al. |
| 5,520,177 A | 5/1996 | Ogawa et al. | 5,766,131 A * | 6/1998 | Kondo et al. ............... 600/502 |
| 5,521,851 A | 5/1996 | Wei et al. | 5,769,785 A | 6/1998 | Diab et al. |
| 5,522,388 A | 6/1996 | Ishikawa et al. | 5,772,587 A | 6/1998 | Gratton et al. |
| 5,524,617 A | 6/1996 | Mannheimer | 5,774,213 A | 6/1998 | Trebino et al. |
| 5,529,064 A | 6/1996 | Rall et al. | 5,776,058 A | 7/1998 | Levinson et al. |
| 5,533,507 A | 7/1996 | Potratz et al. | 5,776,059 A | 7/1998 | Kaestle |
| 5,551,423 A | 9/1996 | Sugiura | 5,779,630 A | 7/1998 | Fein et al. |
| 5,551,424 A | 9/1996 | Morrison et al. | 5,779,631 A | 7/1998 | Chance |
| 5,553,614 A | 9/1996 | Chance | 5,782,237 A | 7/1998 | Casciani et al. |
| 5,553,615 A | 9/1996 | Carim et al. | 5,782,756 A | 7/1998 | Mannheimer |
| 5,555,882 A | 9/1996 | Richardson et al. | 5,782,757 A | 7/1998 | Diab et al. |

| | | | | | |
|---|---|---|---|---|---|
| 5,782,758 A | 7/1998 | Ausec et al. | 5,971,930 A | 10/1999 | Elghazzawi |
| 5,786,592 A | 7/1998 | Hök | 5,978,691 A | 11/1999 | Mills |
| 5,788,634 A | 8/1998 | Suda et al. | 5,978,693 A | 11/1999 | Hamilton et al. |
| 5,790,729 A | 8/1998 | Pologe et al. | 5,983,120 A | 11/1999 | Groner et al. |
| 5,792,052 A | 8/1998 | Isaacson et al. | 5,983,122 A | 11/1999 | Jarman et al. |
| 5,795,292 A | 8/1998 | Lewis et al. | 5,987,343 A | 11/1999 | Kinast |
| 5,797,841 A | 8/1998 | DeLonzor et al. | 5,991,648 A | 11/1999 | Levin |
| 5,800,348 A | 9/1998 | Kaestle | 5,995,855 A | 11/1999 | Kiani et al. |
| 5,800,349 A | 9/1998 | Isaacson et al. | 5,995,856 A | 11/1999 | Mannheimer et al. |
| 5,803,910 A | 9/1998 | Potratz | 5,995,858 A | 11/1999 | Kinast |
| 5,807,246 A | 9/1998 | Sakaguchi et al. | 5,995,859 A | 11/1999 | Takahashi |
| 5,807,247 A | 9/1998 | Merchant et al. | 5,997,343 A | 12/1999 | Mills et al. |
| 5,807,248 A | 9/1998 | Mills | 5,999,834 A | 12/1999 | Wang et al. |
| 5,810,723 A | 9/1998 | Aldrich | 6,002,952 A | 12/1999 | Diab et al. |
| 5,810,724 A | 9/1998 | Gronvall | 6,005,658 A | 12/1999 | Kaluza et al. |
| 5,813,980 A | 9/1998 | Levinson et al. | 6,006,120 A | 12/1999 | Levin |
| 5,817,008 A | 10/1998 | Rafert et al. | 6,011,985 A | 1/2000 | Athan et al. |
| 5,817,009 A | 10/1998 | Rosenheimer et al. | 6,011,986 A | 1/2000 | Diab et al. |
| 5,817,010 A | 10/1998 | Hibl | 6,014,576 A | 1/2000 | Raley et al. |
| 5,818,985 A | 10/1998 | Merchant et al. | 6,018,673 A | 1/2000 | Chin et al. |
| 5,820,550 A | 10/1998 | Polson et al. | 6,018,674 A | 1/2000 | Aronow |
| 5,823,950 A | 10/1998 | Diab et al. | 6,022,321 A | 2/2000 | Amano et al. |
| 5,823,952 A | 10/1998 | Levinson et al. | 6,023,541 A | 2/2000 | Merchant et al. |
| 5,827,179 A | 10/1998 | Lichter et al. | 6,026,312 A | 2/2000 | Shemwell et al. |
| 5,827,182 A | 10/1998 | Raley et al. | 6,026,314 A | 2/2000 | Amerov et al. |
| 5,829,439 A | 11/1998 | Yokosawa et al. | 6,031,603 A | 2/2000 | Fine et al. |
| 5,830,135 A | 11/1998 | Bosque et al. | 6,035,223 A | 3/2000 | Baker, Jr. |
| 5,830,136 A | 11/1998 | DeLonzor et al. | 6,036,642 A | 3/2000 | Diab et al. |
| 5,830,137 A | 11/1998 | Scharf | 6,041,247 A | 3/2000 | Weckstrom et al. |
| 5,839,439 A | 11/1998 | Nierlich et al. | 6,044,283 A | 3/2000 | Fein et al. |
| RE036,000 E | 12/1998 | Swedlow et al. | 6,047,201 A | 4/2000 | Jackson, III |
| 5,842,979 A | 12/1998 | Jarman et al. | 6,055,447 A | 4/2000 | Well |
| 5,842,981 A | 12/1998 | Larsen et al. | 6,061,584 A | 5/2000 | Lovejoy et al. |
| 5,842,982 A | 12/1998 | Mannheimer | 6,064,898 A | 5/2000 | Aldrich |
| 5,846,190 A | 12/1998 | Woehrle | 6,064,899 A | 5/2000 | Fein et al. |
| 5,851,178 A | 12/1998 | Aronow | 6,067,462 A | 5/2000 | Diab et al. |
| 5,851,179 A | 12/1998 | Ritson et al. | 6,073,038 A | 6/2000 | Wang et al. |
| 5,853,364 A | 12/1998 | Baker, Jr. et al. | 6,078,829 A | 6/2000 | Uchida |
| 5,860,919 A | 1/1999 | Kiani-Azarbayjany et al. | 6,078,833 A | 6/2000 | Hueber |
| 5,865,736 A | 2/1999 | Baker, Jr. et al. | 6,081,735 A | 6/2000 | Diab et al. |
| 5,879,294 A | 3/1999 | Anderson et al. | 6,083,157 A | 7/2000 | Noller |
| 5,885,213 A | 3/1999 | Richardson et al. | 6,083,172 A | 7/2000 | Baker, Jr. et al. |
| 5,890,929 A | 4/1999 | Mills et al. | 6,088,607 A | 7/2000 | Diab et al. |
| 5,891,021 A | 4/1999 | Dillon et al. | 6,094,592 A | 7/2000 | Yorkey et al. |
| 5,891,022 A | 4/1999 | Pologe | 6,095,974 A | 8/2000 | Shemwell et al. |
| 5,891,024 A | 4/1999 | Jarman et al. | 6,104,938 A | 8/2000 | Huiku et al. |
| 5,891,025 A | 4/1999 | Buschmann et al. | 6,104,939 A | 8/2000 | Groner |
| 5,891,026 A | 4/1999 | Wang et al. | 6,112,107 A | 8/2000 | Hannula |
| 5,902,235 A | 5/1999 | Lewis et al. | 6,113,541 A | 9/2000 | Dias et al. |
| 5,910,108 A | 6/1999 | Solenberger | 6,115,621 A | 9/2000 | Chin |
| 5,911,690 A | 6/1999 | Rall | 6,122,535 A | 9/2000 | Kaestle et al. |
| 5,912,656 A | 6/1999 | Tham et al. | 6,133,994 A | 10/2000 | Mathews et al. |
| 5,913,819 A | 6/1999 | Taylor et al. | 6,135,952 A | 10/2000 | Coetzee |
| 5,916,154 A | 6/1999 | Hobbs et al. | 6,144,444 A | 11/2000 | Haworth et al. |
| 5,916,155 A | 6/1999 | Levinson et al. | 6,144,867 A | 11/2000 | Walker et al. |
| 5,919,133 A | 7/1999 | Taylor et al. | 6,144,868 A | 11/2000 | Parker |
| 5,919,134 A | 7/1999 | Diab | 6,149,481 A | 11/2000 | Wang et al. |
| 5,920,263 A | 7/1999 | Huttenhoff et al. | 6,151,107 A | 11/2000 | Schöllerman et al. |
| 5,921,921 A | 7/1999 | Potratz et al. | 6,151,516 A | 11/2000 | Kiani-Azarbayjani et al. |
| 5,922,607 A | 7/1999 | Bernreuter | 6,151,518 A | 11/2000 | Hayashi |
| 5,924,979 A | 7/1999 | Swedlow et al. | 6,152,754 A | 11/2000 | Gerhardt et al. |
| 5,924,980 A | 7/1999 | Coetzee | 6,154,667 A | 11/2000 | Miura et al. |
| 5,924,982 A | 7/1999 | Chin | 6,157,850 A | 12/2000 | Diab et al. |
| 5,924,985 A | 7/1999 | Jones | 6,159,147 A | 12/2000 | Lichter et al. |
| 5,934,277 A | 8/1999 | Mortz | 6,163,715 A | 12/2000 | Larsen et al. |
| 5,934,925 A | 8/1999 | Tobler et al. | 6,165,005 A | 12/2000 | Mills et al. |
| 5,940,182 A | 8/1999 | Lepper, Jr. et al. | 6,173,196 B1 | 1/2001 | Delonzor et al. |
| 5,954,644 A | 9/1999 | Dettling et al. | 6,178,343 B1 | 1/2001 | Bindszus et al. |
| 5,957,840 A | 9/1999 | Terasawa et al. | 6,179,159 B1 | 1/2001 | Gurley |
| 5,960,610 A | 10/1999 | Levinson et al. | 6,181,958 B1 | 1/2001 | Steuer et al. |
| 5,961,450 A | 10/1999 | Merchant et al. | 6,181,959 B1 | 1/2001 | Schöllerman et al. |
| 5,961,452 A | 10/1999 | Chung et al. | 6,184,521 B1 | 2/2001 | Coffin, IV et al. |
| 5,964,701 A | 10/1999 | Asada et al. | 6,188,470 B1 | 2/2001 | Grace |

| | | |
|---|---|---|
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grinblatov |
| 6,263,221 B1 | 7/2001 | Chance et al. |
| 6,263,222 B1 | 7/2001 | Diab et al. |
| 6,263,223 B1 | 7/2001 | Sheperd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenstner |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |

| Patent No. | Date | Inventor |
|---|---|---|
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B1 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE038,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |
| 6,714,804 B2 | 3/2004 | Al-Ali et al. |
| 6,714,805 B2 | 3/2004 | Jeon et al. |
| RE038,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,266 B2 | 11/2004 | Varshneya |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,967,652 B1 | 11/2005 | Nubling et al. |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |

| Patent/Pub No. | Date | Inventor |
|---|---|---|
| 7,027,849 B2 | 4/2006 | Al-Ali |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boas et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,112,175 B2 | 9/2006 | Gopinathan et al. |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Kenagy et al. |
| 7,142,901 B2 | 11/2006 | Kiani et al. |
| 7,161,484 B2 | 1/2007 | Tsoukalis |
| 7,162,288 B2 | 1/2007 | Nordstrom et al. |
| 7,164,938 B2 | 1/2007 | Geddes et al. |
| 7,190,986 B1 | 3/2007 | Hannula et al. |
| 7,190,987 B2 | 3/2007 | Kindekugel et al. |
| 7,198,778 B2 | 4/2007 | Achilefu et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,811 B2 | 6/2007 | Schmitt et al. |
| 7,245,953 B1 | 7/2007 | Parker |
| 7,248,910 B2 | 7/2007 | Li et al. |
| 7,254,433 B2 | 8/2007 | Diab et al. |
| 7,254,434 B2 | 8/2007 | Schulz et al. |
| 7,257,438 B2 | 8/2007 | Kinast |
| 7,263,396 B2 | 8/2007 | Chen et al. |
| 7,272,425 B2 | 9/2007 | Al-Ali |
| 7,280,858 B2 | 10/2007 | Al-Ali et al. |
| 7,292,150 B2 | 11/2007 | Shaw |
| 7,295,866 B2 | 11/2007 | Al-Ali |
| 7,297,119 B2 | 11/2007 | Westbrook et al. |
| 7,305,262 B2 | 12/2007 | Brodnick et al. |
| 7,315,753 B2 | 1/2008 | Baker, Jr. et al. |
| 7,341,559 B2 | 3/2008 | Schulz et al. |
| 7,341,560 B2 | 3/2008 | Henderson et al. |
| 7,359,742 B2 | 4/2008 | Maser et al. |
| 7,412,272 B2 | 8/2008 | Medina et al. |
| 7,433,726 B2 | 10/2008 | Perkins |
| 2002/0016537 A1 | 2/2002 | Muz et al. |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0082488 A1* | 6/2002 | Al-Ali et al. ............... 600/323 |
| 2002/0103423 A1 | 8/2002 | Chin et al. |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0171662 A1 | 9/2003 | O'Connor et al. |
| 2003/0181796 A1* | 9/2003 | Pologe ............... 600/322 |
| 2003/0181799 A1 | 9/2003 | Lindekugel et al. |
| 2003/0187337 A1 | 10/2003 | Tarassenko et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2004/0006261 A1 | 1/2004 | Swedlow et al. |
| 2004/0024326 A1 | 2/2004 | Yeo et al. |
| 2004/0039272 A1 | 2/2004 | Abdul-Hafiz et al. |
| 2004/0039273 A1 | 2/2004 | Terry |
| 2004/0054291 A1 | 3/2004 | Schulz et al. |
| 2004/0068164 A1 | 4/2004 | Diab et al. |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0117891 A1 | 6/2004 | Hannula et al. |
| 2004/0122302 A1 | 6/2004 | Mason et al. |
| 2004/0133088 A1 | 7/2004 | Al-Ali |
| 2004/0143172 A1 | 7/2004 | Fudge et al. |
| 2004/0147821 A1 | 7/2004 | Al-Ali et al. |
| 2004/0147824 A1 | 7/2004 | Diab et al. |
| 2004/0158134 A1 | 8/2004 | Diab et al. |
| 2004/0162472 A1 | 8/2004 | Berson et al. |
| 2004/0167381 A1 | 8/2004 | Lichter |
| 2004/0186358 A1 | 9/2004 | Chernow et al. |
| 2004/0199063 A1 | 10/2004 | O'Neil et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215085 A1 | 10/2004 | Schnall |
| 2004/0236196 A1 | 11/2004 | Diab et al. |
| 2004/0257557 A1 | 12/2004 | Block |
| 2004/0260161 A1 | 12/2004 | Melker et al. |
| 2005/0004479 A1 | 1/2005 | Townsend et al. |
| 2005/0014999 A1 | 1/2005 | Rahe-Meyer |
| 2005/0017864 A1 | 1/2005 | Banet |
| 2005/0020887 A1 | 1/2005 | Goldberg |
| 2005/0033131 A1 | 2/2005 | Chen |
| 2005/0043599 A1 | 2/2005 | O'Mara |
| 2005/0043600 A1 | 2/2005 | Diab et al. |
| 2005/0049468 A1 | 3/2005 | Carlson |
| 2005/0049471 A1 | 3/2005 | Aceti et al. |
| 2005/0059869 A1 | 3/2005 | Scharf et al. |
| 2005/0059870 A1 | 3/2005 | Aceti |
| 2005/0070773 A1 | 3/2005 | Chin |
| 2005/0075546 A1 | 4/2005 | Samsoondar |
| 2005/0075550 A1 | 4/2005 | Lindekugel |
| 2005/0085704 A1 | 4/2005 | Schulz |
| 2005/0090720 A1 | 4/2005 | Wu |
| 2005/0119538 A1 | 6/2005 | Jeon et al. |
| 2005/0163412 A1 | 7/2005 | Glebov et al. |
| 2005/0197548 A1 | 9/2005 | Dietiker |
| 2005/0228248 A1 | 10/2005 | Dietiker |
| 2005/0228299 A1 | 10/2005 | Banet |
| 2005/0228300 A1 | 10/2005 | Jaime et al. |
| 2005/0256386 A1 | 11/2005 | Chan |
| 2005/0272986 A1 | 12/2005 | Smith |
| 2005/0277819 A1 | 12/2005 | Kiani et al. |
| 2005/0283082 A1 | 12/2005 | Geddes et al. |
| 2006/0020179 A1 | 1/2006 | Anderson |
| 2006/0030764 A1 | 2/2006 | Porges |
| 2006/0036136 A1 | 2/2006 | Shaw |
| 2006/0058594 A1 | 3/2006 | Ishizuka et al. |
| 2006/0058690 A1 | 3/2006 | Bartnik |
| 2006/0064024 A1 | 3/2006 | Schnall |
| 2006/0069319 A1 | 3/2006 | Elhag et al. |
| 2006/0074280 A1 | 4/2006 | Martis |
| 2006/0075257 A1 | 4/2006 | Martis et al. |
| 2006/0079794 A1 | 4/2006 | Liu et al. |

| | | | | | | |
|---|---|---|---|---|---|---|
| 2006/0084852 | A1 | 4/2006 | Mason et al. | EP | 01006864 | 10/1998 |
| 2006/0084878 | A1 | 4/2006 | Banet | EP | 0875199 | 11/1998 |
| 2006/0089547 | A1 | 4/2006 | Sarussi | EP | 00998214 | 12/1998 |
| 2006/0106294 | A1 | 5/2006 | Maser et al. | EP | 0 898 933 | 3/1999 |
| 2006/0122517 | A1 | 6/2006 | Banet | EP | 0898933 | 3/1999 |
| 2006/0129039 | A1 | 6/2006 | Lindner | EP | 01332713 | 8/2003 |
| 2006/0149149 | A1 | 7/2006 | Schmid | EP | 01469773 | 8/2003 |
| 2006/0155198 | A1 | 7/2006 | Schmid | EP | 1502529 | 7/2004 |
| 2006/0173257 | A1 | 8/2006 | Nagai | EP | 01491135 | 12/2004 |
| 2007/0032708 | A1 | 2/2007 | Eghbal et al. | EP | 1491135 | 12/2004 |
| 2007/0032709 | A1 | 2/2007 | Coakley et al. | FR | 2685865 | 1/1992 |
| 2007/0032710 | A1 | 2/2007 | Raridan et al. | GB | 2 259 545 | 3/1993 |
| 2007/0032712 | A1 | 2/2007 | Raridan et al. | JP | 63275325 | 11/1988 |
| 2007/0032715 | A1 | 2/2007 | Eghbal et al. | JP | 2013450 | 1/1990 |
| 2007/0032716 | A1 | 2/2007 | Raridan et al. | JP | 2111343 | 4/1990 |
| 2007/0060808 | A1 | 3/2007 | Hoarau | JP | 02 191434 | 7/1990 |
| 2007/0073117 | A1 | 3/2007 | Raridan | JP | 2237544 | 9/1990 |
| 2007/0073121 | A1 | 3/2007 | Hoarau et al. | JP | 03 173536 | 7/1991 |
| 2007/0073122 | A1 | 3/2007 | Hoarau | JP | 3170866 | 7/1991 |
| 2007/0073123 | A1 | 3/2007 | Raridan | JP | 3245042 | 10/1991 |
| 2007/0073125 | A1 | 3/2007 | Hoarau et al. | JP | 4174648 | 6/1992 |
| 2007/0073126 | A1 | 3/2007 | Raridan | JP | 4191642 | 7/1992 |
| 2007/0073128 | A1 | 3/2007 | Hoarau | JP | 4332536 | 11/1992 |
| 2007/0078309 | A1 | 4/2007 | Matlock | JP | 3124073 | 3/1993 |
| 2007/0078316 | A1 | 4/2007 | Hoarau | JP | 5049624 | 3/1993 |
| 2007/0078317 | A1 | 4/2007 | Matlock | JP | 5049625 | 3/1993 |
| 2007/0260129 | A1 | 11/2007 | Chin | JP | 3115374 | 4/1993 |
| 2007/0260130 | A1 | 11/2007 | Chin | JP | 05 200031 | 8/1993 |
| 2007/0260131 | A1 | 11/2007 | Chin | JP | 2005/200031 | 8/1993 |
| 2007/0299328 | A1 | 12/2007 | Chin et al. | JP | 5212016 | 8/1993 |
| | | | | JP | 06 014906 | 1/1994 |
| FOREIGN PATENT DOCUMENTS | | | | JP | 06014906 | 1/1994 |
| DE | 3516338 | | 11/1986 | JP | 6016774 | 3/1994 |
| DE | 37 03 458 | | 8/1988 | JP | 3116255 | 4/1994 |
| DE | 3938759 | | 5/1991 | JP | 6029504 | 4/1994 |
| DE | 4210102 | | 9/1993 | JP | 6098881 | 4/1994 |
| DE | 4423597 | | 8/1995 | JP | 06 154177 | 6/1994 |
| DE | 19632361 | | 2/1997 | JP | 6269430 | 9/1994 |
| DE | 69123448 | | 5/1997 | JP | 6285048 | 10/1994 |
| DE | 19703220 | | 7/1997 | JP | 7001273 | 1/1995 |
| DE | 19640807 | | 9/1997 | JP | 7124138 | 5/1995 |
| DE | 19647877 | | 4/1998 | JP | 7136150 | 5/1995 |
| DE | 10030862 | | 1/2002 | JP | 3116259 | 6/1995 |
| DE | 10030862 | A1 | 1/2002 | JP | 3116260 | 6/1995 |
| DE | 20318882 | | 4/2004 | JP | 7155311 | 6/1995 |
| EP | 0127947 | | 5/1984 | JP | 7155313 | 6/1995 |
| EP | 00194105 | | 9/1986 | JP | 3238813 | 7/1995 |
| EP | 00204459 | | 12/1986 | JP | 7171139 | 7/1995 |
| EP | 204459 | | 12/1986 | JP | 3134144 | 9/1995 |
| EP | 0 262 779 | | 4/1988 | JP | 7236625 | 9/1995 |
| EP | 0315040 | | 10/1988 | JP | 7246191 | 9/1995 |
| EP | 0314331 | | 5/1989 | JP | 8256996 | 10/1996 |
| EP | 00352923 | | 1/1990 | JP | 9192120 | 7/1997 |
| EP | 0 360 977 | | 4/1990 | JP | 10216113 | 8/1998 |
| EP | 430340 | | 6/1991 | JP | 10216114 | 8/1998 |
| EP | 00430340 | | 6/1991 | JP | 10216115 | 8/1998 |
| EP | 0435 500 | | 7/1991 | JP | 10337282 | 12/1998 |
| EP | 0572684 | | 5/1992 | JP | 11019074 | 1/1999 |
| EP | 00497021 | | 8/1992 | JP | 11155841 | 6/1999 |
| EP | 0529412 | | 8/1992 | JP | 11 188019 | 7/1999 |
| EP | 0531631 | | 9/1992 | JP | 11244268 | 9/1999 |
| EP | 0566354 | | 4/1993 | JP | 20107157 | 4/2000 |
| EP | 0587009 | | 8/1993 | JP | 20237170 | 9/2000 |
| EP | 00630203 | | 9/1993 | JP | 21245871 | 9/2001 |
| EP | 0 572 684 | | 12/1993 | JP | 22224088 | 8/2002 |
| EP | 00615723 | | 9/1994 | JP | 22282242 | 10/2002 |
| EP | 00702931 | | 3/1996 | JP | 23153881 | 5/2003 |
| EP | 724860 | | 8/1996 | JP | 23153882 | 5/2003 |
| EP | 00724860 | | 8/1996 | JP | 23169791 | 6/2003 |
| EP | 00793942 | | 9/1997 | JP | 23194714 | 7/2003 |
| EP | 0 864 293 | | 9/1998 | JP | 23210438 | 7/2003 |
| EP | 01006863 | | 10/1998 | JP | 23275192 | 9/2003 |
| | | | | JP | 23339678 | 12/2003 |

| | | |
|---|---|---|
| JP | 24008572 | 1/2004 |
| JP | 24089546 | 3/2004 |
| JP | 24113353 | 4/2004 |
| JP | 24135854 | 5/2004 |
| JP | 24148069 | 5/2004 |
| JP | 24148070 | 5/2004 |
| JP | 24159810 | 6/2004 |
| JP | 24166775 | 6/2004 |
| JP | 24194908 | 7/2004 |
| JP | 24202190 | 7/2004 |
| JP | 24248819 | 9/2004 |
| JP | 24248820 | 9/2004 |
| JP | 24261364 | 9/2004 |
| JP | 24290412 | 10/2004 |
| JP | 24290544 | 10/2004 |
| JP | 24290545 | 10/2004 |
| JP | 24329406 | 11/2004 |
| JP | 24329607 | 11/2004 |
| JP | 24329928 | 11/2004 |
| JP | 24337605 | 12/2004 |
| JP | 24344367 | 12/2004 |
| JP | 24351107 | 12/2004 |
| JP | 25034472 | 2/2005 |
| JP | 25052385 | 3/2005 |
| JP | 25110816 | 4/2005 |
| JP | 25111161 | 4/2005 |
| JP | 25125106 | 5/2005 |
| JP | 25168600 | 6/2005 |
| WO | WO 89/09566 | 10/1989 |
| WO | WO 90/01293 | 2/1990 |
| WO | WO9001293 | 2/1990 |
| WO | WO 90/04352 | 5/1990 |
| WO | WO 91/01678 | 2/1991 |
| WO | WO 91/11137 | 8/1991 |
| WO | WO 92/00513 | 1/1992 |
| WO | WO 92/21281 | 12/1992 |
| WO | WO 93/09711 | 5/1993 |
| WO | WO 93/13706 | 7/1993 |
| WO | WO 93/16629 | 9/1993 |
| WO | WO 94/03102 | 2/1994 |
| WO | WO 94/23643 | 10/1994 |
| WO | WO 95/02358 | 1/1995 |
| WO | WO 95/12349 | 5/1995 |
| WO | WO 95/16970 | 6/1995 |
| WO | WO 96/13208 | 5/1996 |
| WO | WO9616591 | 6/1996 |
| WO | WO 96/39927 | 12/1996 |
| WO | WO 97/36536 | 10/1997 |
| WO | WO 97/36538 | 10/1997 |
| WO | WO 97/49330 | 12/1997 |
| WO | WO 98/17174 | 4/1998 |
| WO | WO 98/18382 | 5/1998 |
| WO | WO 98/43071 | 10/1998 |
| WO | WO 98/51212 | 11/1998 |
| WO | WO 98/57577 | 12/1998 |
| WO | WO 99/00053 | 1/1999 |
| WO | WO 99/32030 | 7/1999 |
| WO | WO 99/47039 | 9/1999 |
| WO | WO 99/63884 | 12/1999 |
| WO | WO 00/21438 | 4/2000 |
| WO | WO 00/28888 | 5/2000 |
| WO | WO 00/59374 | 10/2000 |
| WO | WO 01/13790 | 3/2001 |
| WO | WO 01/16577 | 3/2001 |
| WO | WO 01/17421 | 3/2001 |
| WO | WO 01/47426 | 3/2001 |
| WO | WO 01/40776 | 6/2001 |
| WO | WO 01/67946 | 9/2001 |
| WO | WO 01/76461 | 10/2001 |
| WO | WO 02/14793 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 | 1/2003 |
| WO | WO 03/001180 | 1/2003 |
| WO | WO 03/009750 | 2/2003 |
| WO | WO 03/011127 | 2/2003 |
| WO | WO 03/020129 | 3/2003 |
| WO | WO 03/039326 | 5/2003 |
| WO | WO 03/063697 | 8/2003 |
| WO | WO 03/073924 | 9/2003 |
| WO | WO 04/000114 | 12/2003 |
| WO | WO 2004/006748 | 1/2004 |
| WO | WO 2004/069046 | 8/2004 |
| WO | WO 2004/075746 | 9/2004 |
| WO | WO 2005/002434 | 1/2005 |
| WO | WO 2005/009221 | 2/2005 |
| WO | WO 2005/010567 | 2/2005 |
| WO | WO 2005/010568 | 2/2005 |
| WO | WO 2005/020120 | 3/2005 |
| WO | WO2005053530 | 6/2005 |
| WO | WO 2005/065540 | 7/2005 |

OTHER PUBLICATIONS

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30th—Nov. 2nd, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four•Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002; pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisam, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 24392442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

* cited by examiner

CLIP-STYLE MEDICAL SENSOR AND TECHNIQUE FOR USING THE SAME

BACKGROUND OF THE INVENTION

1. Field of the Invention

The present invention relates generally to medical devices and, more particularly, to sensors used for sensing physiological parameters of a patient.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics. Such devices provide doctors and other healthcare personnel with the information they need to provide the best possible healthcare for their patients. As a result, such monitoring devices have become an indispensable part of modem medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

In many instances, it may be desirable to employ, for cost and/or convenience, a pulse oximeter sensor that is reusable. Such reusable sensors, however, may be uncomfortable for the patient for various reasons. For example, the materials used in their construction may not be adequately compliant or supple or the structural features may include angles or edges.

Furthermore, the reusable sensor should fit snugly enough that incidental patient motion will not dislodge or move the sensor, yet not so tight that it may interfere with pulse oximetry measurements. Such a conforming fit may be difficult to achieve over a range of patient physiologies without adjustment or excessive attention on the part of medical personnel. In addition, lack of a tight or secure fit may allow light from the environment to reach the photodetecting elements of the sensor. Such environmental light is not related to a physiological characteristic of the patient and may, therefore, introduce error into the measurements derived using data obtained with the sensor.

Reusable pulse oximeter sensors are also used repeatedly and, typically, on more than one patient. Therefore, over the life of the sensor, detritus and other bio-debris (sloughed off skin cells, dried fluids, dirt, and so forth) may accumulate on the surface of the sensor or in crevices and cavities of the sensor, after repeated uses. As a result, it may be desirable to quickly and/or routinely clean the sensor in a thorough manner. However, in sensors having a multi-part construction, as is typical in reusable pulse oximeter sensors, it may be difficult to perform such a quick and/or routine cleaning. For example, such a thorough cleaning may require disassembly of the sensor and individual cleaning of the disassembled parts or may require careful cleaning using utensils capable of reaching into cavities or crevices of the sensor. Such cleaning is labor intensive and may be impractical in a typical hospital or clinic environment.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body comprising a first portion and a second portion; at least one sensing element disposed on the sensor body; and a sliding clip adapted to slide along the sensor body to bias the first portion towards the second portion.

There is also provided a sensor that includes: a sensor body comprising a first portion and a second portion; at least one sensing element disposed on the sensor body; and a sliding mechanism adapted to move between an engaged position and a disengaged position, wherein the first portion and the second portion are biased towards one another when the sliding mechanism is in the engaged position.

There is also provided a pulse oximetry system that includes: a pulse oximetry monitor; and a pulse oximetry sensor adapted to be operatively coupled to the monitor, the sensor including: a sensor body comprising a first portion and a second portion; at least one sensing element disposed on the sensor body; and a sliding clip adapted to slide along the sensor body to bias the first portion towards the second portion.

There is also provided a method of manufacturing a sensor, the method including:

providing a sensor body comprising a first portion and a second portion and at least one sensing element; and providing a sliding clip adapted to slide along the sensor body to bias the first portion towards the second portion.

There is also provided a method of applying a sensor, the method including:

inserting a patient's tissue into a sensor body having at least one sensing element; and sliding a clip into an engaged position. There is also provided a sensor kit, the kit comprising: a first sensor body having a first size, the first sensor body comprising: a first portion and a second portion; at least one sensing element disposed on the first sensor body; a second sensor body having a second size, the second sensor body comprising: a first portion and a second portion; at least one sensing element disposed on the second sensor body; and at least one detachable clip, wherein the detachable clip is adapted to slide along the first sensor body or the second sensor body.

There is also provided a sensor kit, the kit comprising: A pulse oximetry sensor kit, comprising: at least one sensor body comprising: a first portion and a second portion; at least one sensing element disposed on the sensor body; a first detachable clip having a first size, wherein the detachable clip is adapted to bias the first portion towards the second portion; and a second detachable clip having a second size, wherein the second detachable clip is adapted to bias the first portion towards the second portion.

There is also provided a sensor that includes a sensor body comprising a first portion and a second portion; at least one sensing element disposed on the sensor body; and a detachable clip adapted to bias the first portion towards the second portion.

There is also provided a pulse oximetry system that includes: a pulse oximeter monitor; and a pulse oximetry sensor configured to communicate with the pulse oximetry monitor, the pulse oximetry sensor comprising: a sensor body comprising a first portion and a second portion; at least one sensing element disposed on the sensor body; and a detachable clip adapted to bias the first portion towards the second portion.

There is also provided a method of manufacturing a sensor that includes: providing a sensor body comprising a first portion and a second portion and having at least one sensing element disposed thereon; and providing a detachable clip adapted to bias the first portion towards the second portion.

There is also provided a method that includes: inserting a patient's tissue into a sensor body having a first portion and a second portion and at least one sensing element; and applying a detachable clip to the sensor body to bias the first portion towards the second portion.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a reusable sensor for pulse oximetry or other applications utilizing spectrophotometry that is easily cleaned, comfortable, and easy to apply to a patient. In accordance with the present technique, a reusable clip-style sensor is provided that includes a sliding or removable mechanism, such as a metal flat spring or a torsion spring, providing a closing bias to allow the sensor to be placed securely on a patient. In accordance with some aspects of the present techniques, the reusable clip-style sensor is configured to provide patient comfort and a suitably conformable fit over a wide variety of patient sizes.

Pulse oximetry sensors are typically placed on a patient in a location that is normally perfused with arterial blood to facilitate measurement of the desired blood characteristics, such as arterial oxygen saturation measurement ($SpO_2$). Common sensor sites include a patient's fingertips, toes, or earlobes. Regardless of the placement of a pulse oximetry sensor 10, the reliability of the pulse oximetry measurement is related to the accurate detection of transmitted light that has passed through the perfused tissue. Hence, a sensor 10 that fits a patient securely may reduce movement of the sensor or infiltration of light from outside sources into the sensor, and thus may provide more accurate pulse oximetry measurements.

Figure 1A:
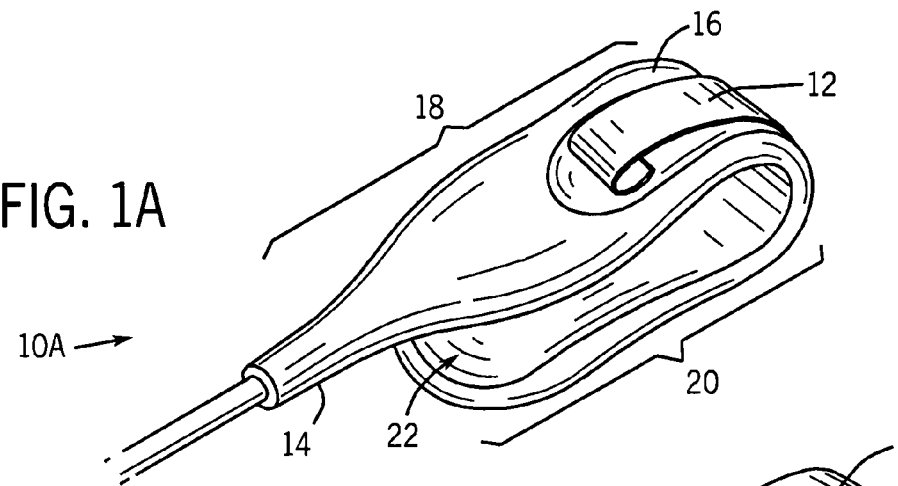
FIG. 1A illustrates a perspective view of an exemplary sensor with an engaged sliding flat spring for use in a pulse oximetry sensor, in accordance with aspects of the present technique.
Figure 1B:
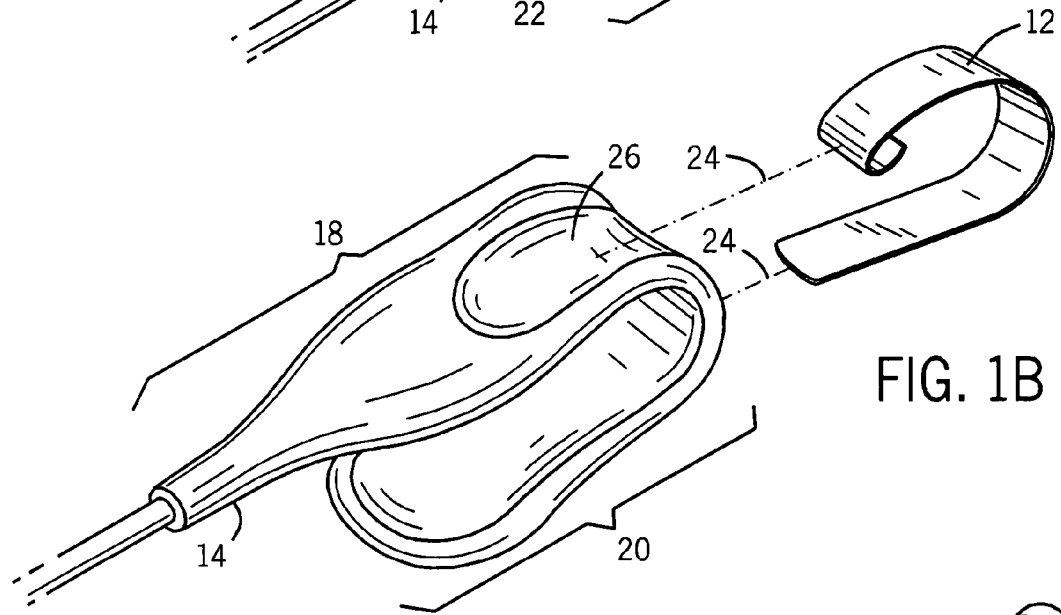
FIG. 1B illustrates a perspective view of the sensor of FIG. 1A in which the sliding flat spring is in the disengaged position.

Referring now to FIG. 1A and FIG. 1B, an exemplary sensor 10A is depicted having an external flat spring 12. FIG. 1A illustrates a perspective view of a sensor 10A with an external flat spring 12 in the closed, or engaged, position. The flat spring 12 is fitted at or near the end of the sensor body 14 that is opposite from where the finger, toe, or other patient appendage is inserted into the assembled sensor. The flat spring 12 may be slidably disposed on a surface 16 of the sensor body 14 that does not contact the tissue during normal use. In the depicted embodiment, the flat spring 12 (or other biasing mechanism) provides or contributes to a closing force applied to a first portion 18 and a second portion 20 of the sensor body such that the first portion 18 and second portion 20 are pushed together when the flat spring 12 is engaged. Thus, after a tissue is inserted into the sensor 10A, the flat spring 12 may slide toward the site 22 of tissue insertion to move the sensor 10A to the closed position. Generally, the sensor 10A is in the closed position when the flat spring 12 is fully flush against the surface 16 of the sensor body 14 that does not contact the tissue during normal use.

FIG. 1B shows the sensor 10A with the flat spring 12 in the open, or disengaged, position. The flat spring 12 may slide along the sensor body 14 along an imaginary axis 24 in order to move the sensor 10A from the closed position to the open position. As depicted, the sensor body 14 has a depression 26 disposed on the surface 16 of the sensor body that does not contact the tissue during normal use. The depression 26 may be suitably sized and shaped to accommodate the flat spring 12, and to allow the flat spring 12 to easily slide between the open position and closed position upon application of manual force. The depression may be disposed on both the first portion 18 and the second portion 20 of the sensor body 14. It is contemplated that the depression 26 may be constructed from or coated with a generally smooth material, such as plastic, to reduce the frictional resistance of the depression 26 against the flat spring 12 as the flat spring 12 moves between the open position and the closed position. As the sensor body 14 may be relatively thinner in the area of a depression 26, it may be advantageous to provide additional support structures disposed on or near the depression 26 designed to cushion the patient tissue from possible discomfort caused by the spring force of the flat spring 12.

Figure 1C:
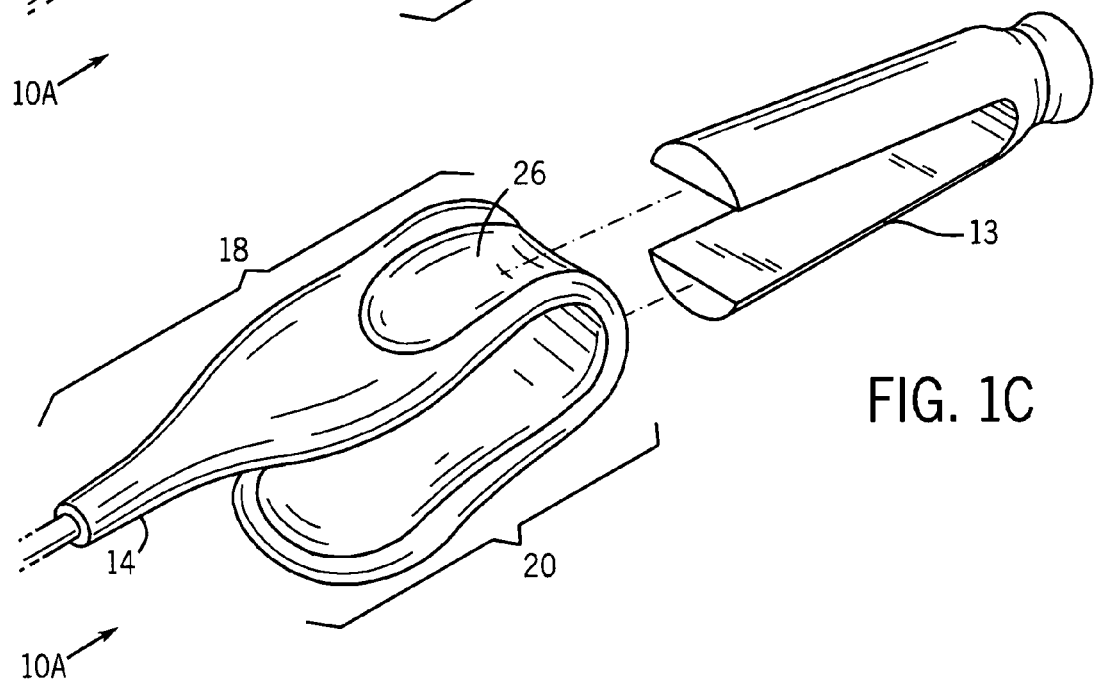
FIG. 1C illustrates a perspective view of the sensor of FIG. 1A in which a clothespin-like clip is in the disengaged position.

FIG. 1C is an alternate embodiment in which the sensor 10A may be closed with a clip 13. The clip 13 may be a removable clothespin-like structure, as depicted, or other structure that may be opened to accommodate the sensor body 14, and closed to provide a closing bias to the first portion 18 and the second portion 20. For example, in certain embodiments, a hinged clip (not shown) may applied to the sensor body 14. In certain embodiments, it may be desirable to affix the sensor 10A to the patient with multiple clips 13 to provide the appropriate closing force at multiple points on the patient's tissue.

Figure 2:
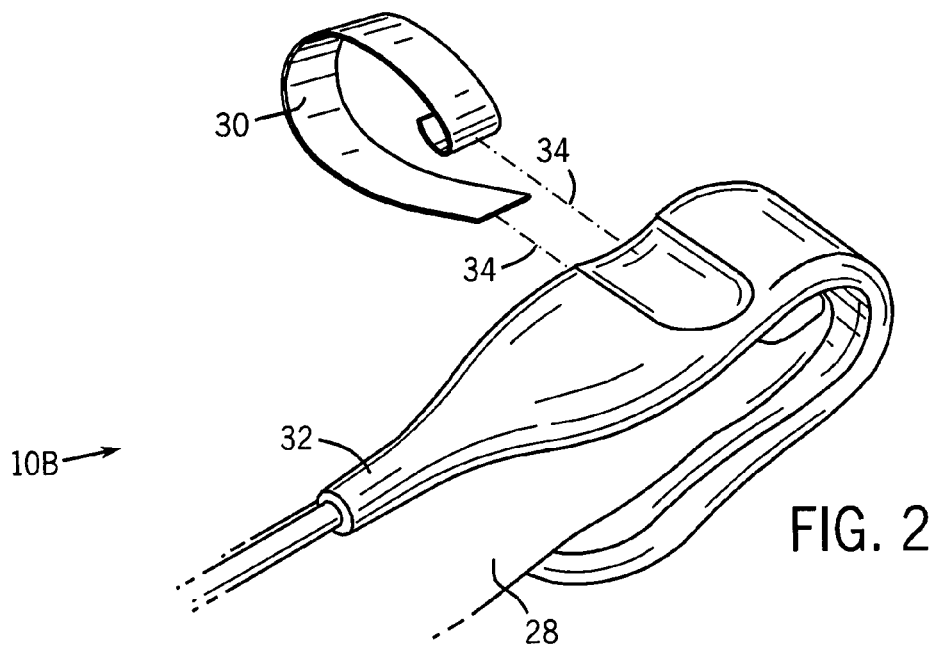
FIG. 2 illustrates a perspective view of an exemplary sensor with a sliding flat spring that slides orthogonally to the site of tissue insertion, in accordance with aspects of the present technique.

FIG. 2 depicts an alternate embodiment of a sensor 10B applied to a patient digit 28 in which a flat spring 30 may be configured to slide along the sensor body 32 on an imaginary axis 34 that is orthogonal to the digit 28. Such an embodiment may be advantageous if a patient experiences discomfort from an alternate sensor arrangement. The flat spring 30 as arranged in the sensor 10B may provide pressure to the tissue in a manner which is more comfortable for the patient. It is contemplated that, in certain embodiments, the flat spring 30 may be arranged along the sensor body 32 in a variety of positions in order to maximize patient comfort.

Figure 3:
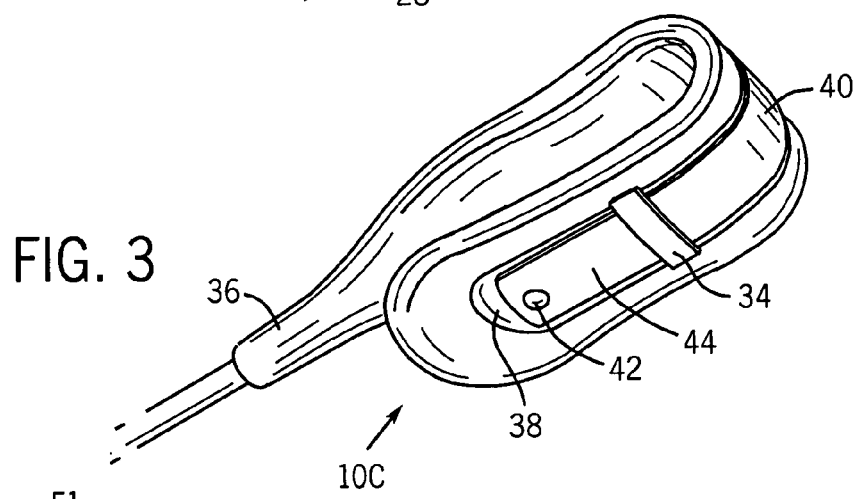
FIG. 3 illustrates a perspective view of an exemplary sensor with a sliding flat spring and a retaining clip and guard, in accordance with aspects of the present technique.

In certain embodiments, it may be advantageous to provide additional guides or restraints to prevent the flat spring from detaching itself from the sensor body during normal use. FIG. 3 illustrates a sensor 10C with a restraining clip 34. The restraining clip 34 is disposed on the sensor body 36 over a depression 38, such that the flat spring 40 slides underneath the restraining clip 34 as it moves from the open position to the closed position. The flat spring 40 may also optionally include a guard 42 disposed on the side 44 of the flat spring 40 that contacts the restraining clip 34 during normal use. The guard 42 is configured to collide with the restraining clip 34 when the flat spring 40 is moved to the open position. The guard 42 prevents further movement of the flat spring 40 along the sensor body 36, and hence prevents the flat spring 40 from being pulled off entirely. The restraining clip 34 and guard 42 may prevent a healthcare worker from inadvertently applying an excess of manual force and pulling the flat spring 40 off the sensor body 36 when moving the flat spring 40 to the open position. In certain embodiments (not shown), the restraining clip 34 may be removable in order to detach the flat clip 40 completely from the sensor body 36. For example, it may be advantageous to remove the flat spring 40 from the sensor body 36 to allow the sensor body 36 to be cleaned.

In general, a sensor body (e.g. sensor body 14, 32, 36, 50, or 56) as described herein may be easily maintained, cleaned, and/or disinfected by immersing the sensor into a disinfectant or cleaning solution or by rinsing the sensor body off, such as under running water. Furthermore, a sensor body as provided herein has a generally simple topography, and may be constructed or molded from a single part. Thus, the sensor body may be free of the irregularities typically associated with a complex multi-part construction which may normally allow the accumulation of biological detritus or residue.

Figure 4:
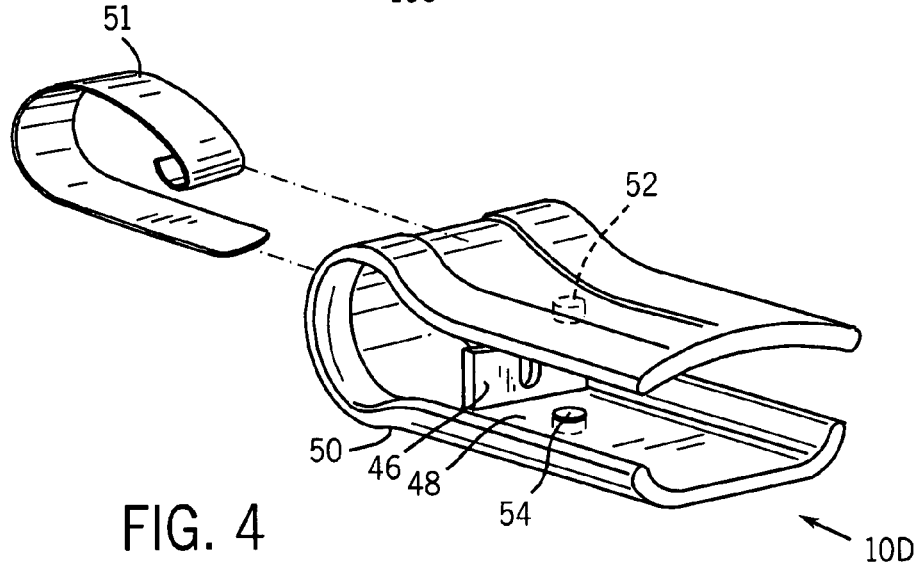
FIG. 4 illustrates a perspective view of an exemplary sensor with a sliding flat spring and a finger stop.

In certain embodiments, the sensors provided by the present techniques may used on patients with a variety of physiologies, such as fingers of varying sizes. Thus, as it is envisioned that a single sensor may be appropriate for use on many different patients, it may be advantageous to provide additional fitting components to ensure that the light emitting and detecting components of the sensor are generally positioned in comparable locations on one patient's tissue as compared to another patient. FIG. 4 illustrates a perspective side view of a sensor 10D with a finger stop 46 on the tissue-contacting surface 48 of the sensor body 50. When a digit is inserted into the sensor 10D, the tip of the digit may be prevented from inserting any further within the sensor body 50 by the finger stop 46. When the digit is inserted as far as possible, the flat spring 51 may then slide into the engaged position to secure the sensor 10D onto the digit. The finger stop 46 will be generally disposed on the tissue-contacting surface 48 of the sensor body 50 to position the emitter 52 and the detector 54 at the desired spot on the patient's tissue.

Figure 5A:
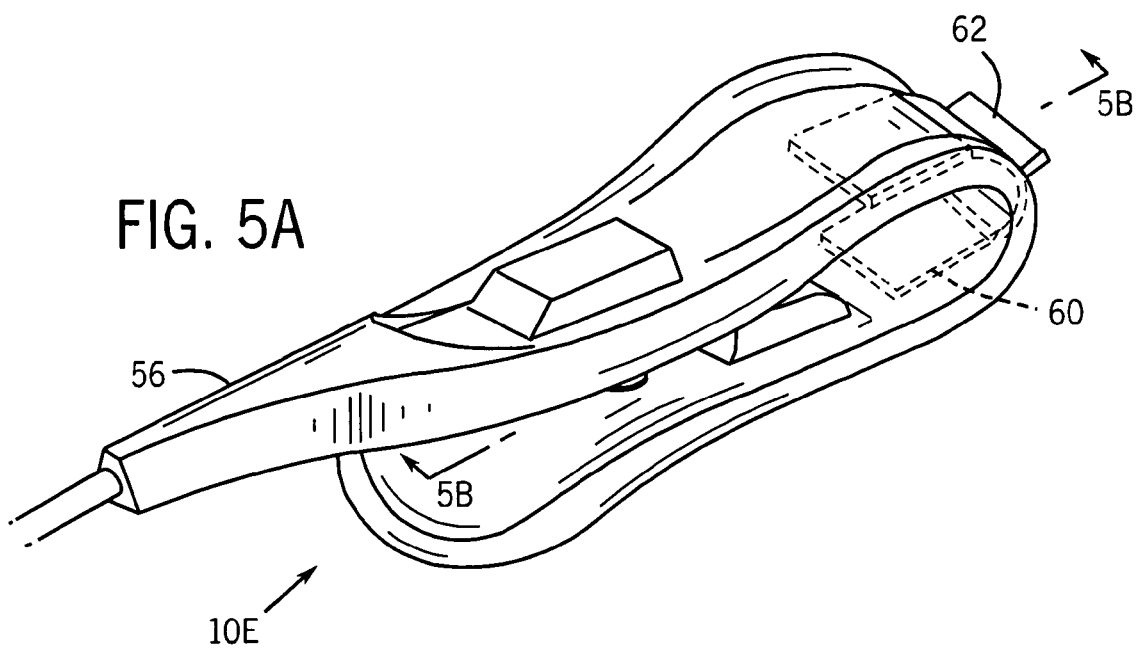
FIG. 5A illustrates a perspective view of an exemplary overmolded sensor with an internal frame and an embedded spring, in accordance with aspects of the present technique.
Figure 5B:
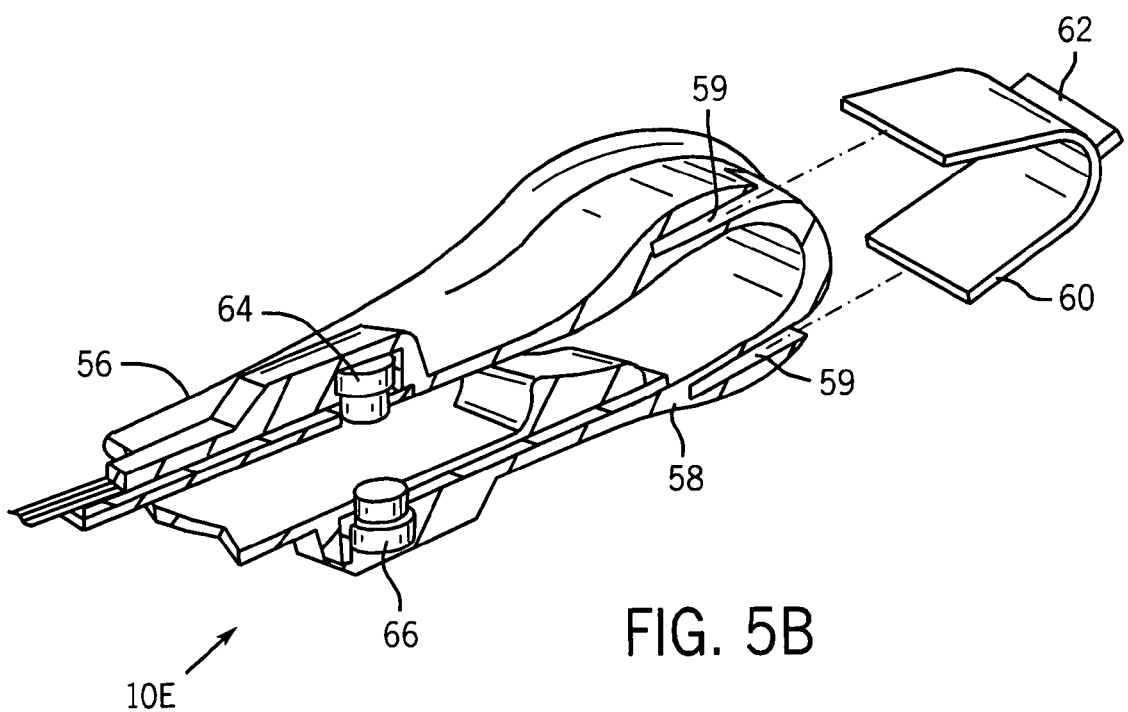
FIG. 5B illustrates a cross-section of the overmolded sensor depicted in FIG. 5A.
Figure 6:
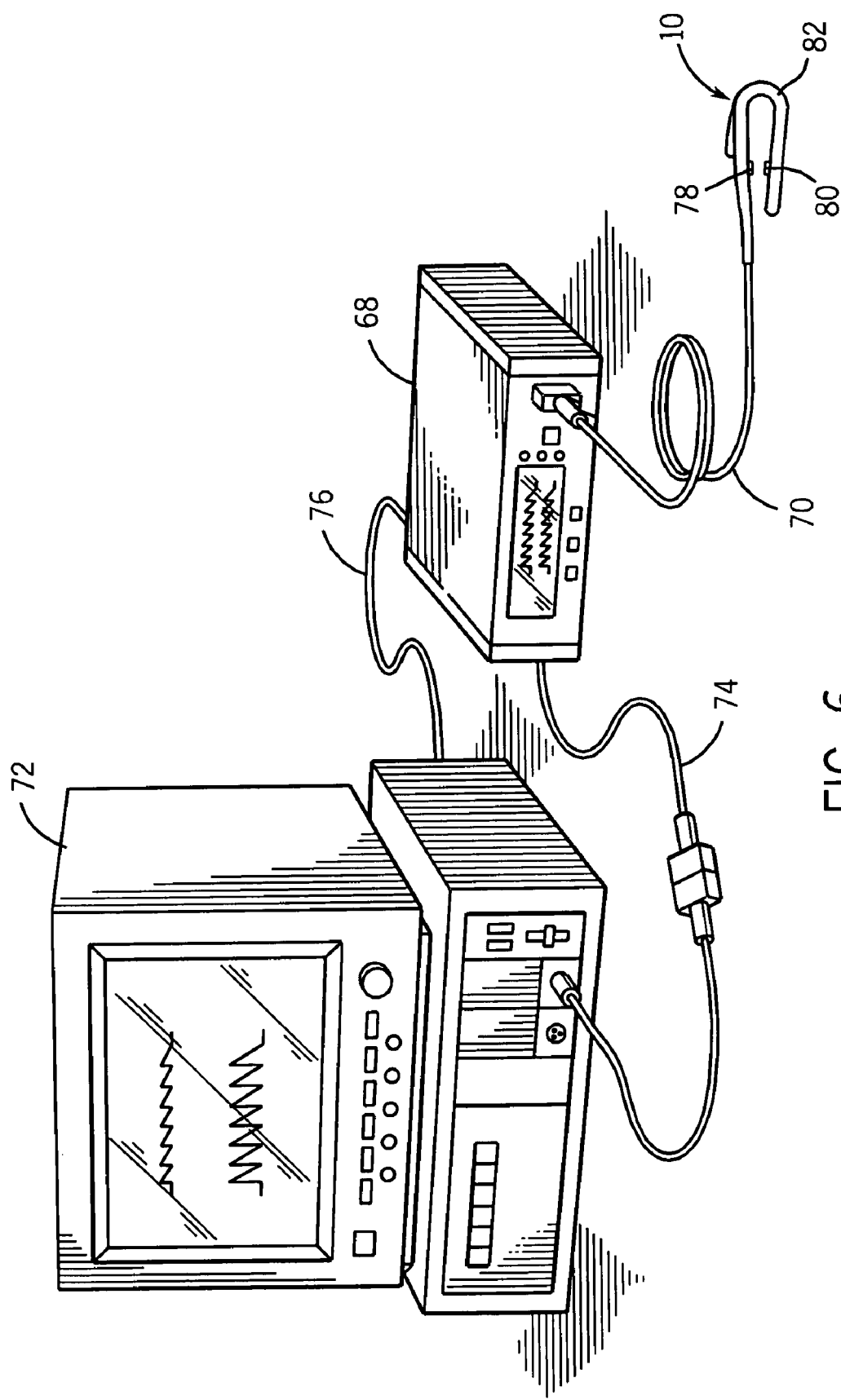
FIG. 6 illustrates a pulse oximetry system coupled to a multi-parameter patient monitor and a pulse oximetry sensor, in accordance with aspects of the present technique.

In certain embodiments, it may be advantageous to embed a sliding clip, such as a flat spring, in the sensor body when the sensor is in the closed position. Such an exemplary sensor 10E is illustrated in FIG. 5A, which depicts an overmolded sensor body 56. FIG. 5B is a cross-sectional view in which an internal frame 58 of the overmolded sensor body 56 is visible. The internal frame 58 provides a skeletal, internal framework for a pulse oximetry sensor 10E. Such a skeletal framework provides structural support for a coating or overmolding. In addition, the internal frame 58 provides support and framework for openings 59 in the overmolded sensor body 56 into which a flat spring 60 may slide. The flat spring 60 is in the closed position, as shown in FIG. 5A, when mostly embedded in the overmolded sensor body 56. When the flat spring 60 is embedded in the overmolded sensor body 56, some sharp edges or corners may be shielded from the patient, and thus the sensor 10E may be more comfortable. It may be also advantageous to include a handle 62 on the flat spring 60 in order to allow the flat spring 60 to be more easily grasped by a user.

In certain embodiments, the internal frame 58 is constructed, in whole or in part, from polymeric materials, such as thermoplastics, or from other suitably rigid or semi-rigid materials, such as stainless steel, aluminum, magnesium, or other metals or alloys which are sufficiently ductile and/or strong. The sensor 10E may be overmolded over the internal frame 58 by an injection molding process. In one example of such a process the internal frame 58 may be positioned within a die or mold of the desired shape for the sensor 10E. The molten or otherwise unset overmold material may then be injected into the die or mold. In certain embodiments, other sensor components, such as the emitter 64 and/or detector 66, may be attached or inserted into their respective housings or positions on the overmolded sensor body. Alternatively, the optical components (such as emitter 64 and detector 66) and/or conductive structures (such as wires or flex circuits) may be placed on the internal frame 58 prior to overmolding.

In one implementation, the sensor body as described herein (e.g. sensor body 14, 32, 36, 50, or 56) may be constructed, either wholly or in part, from a thermoplastic elastomer or other conformable material. In such an embodiment, the conformable nature of the sensor body may serve to accommodate a wide variety of patient tissue sizes. The thermoplastic elastomer may include compositions such as thermoplastic polyolefins, thermoplastic vulcanizate alloys, silicone, polyurethane, and so forth. In one embodiment, the sensor body is constructed from polyurethane having a durometer of 15 Shore A. As will be appreciated by those of ordinary skill in the art, the sensor body may vary, depending on the varying degrees of conformability, durability, wettabiliy, or other physical and/or chemical traits that are desired. Indeed, the sensor body may be selected to provide additional spring force to that provided by a sliding clip or spring, resulting in a combined spring force which includes the force provided by the flat spring and the force provided by the sensor body.

In certain embodiments, the sensor body is formed as a single molded part configured with housings or other structures designed to accommodate the sensor optics. For example, a sensor body as described herein may be configured to include an emitter housing and a detector housing that provide precise positioning of the emitter and detector units when inserted into their respective housings. The sensor body may also provides surfaces, openings, and/or structures for securing conductors (such as wires or flex circuits) that attach to the emitter and/or detector units upon assembly. The sensor body also may provides an external cable guide through which a cable, such as an electrical or optical cable, may pass to connect to the electrical or optical conductors attached to the emitter and/or detector units upon assembly.

A sensor body as described herein may substantially U-shaped or clamshell-shaped. However, it is envisioned that the sensor body may assume any suitable configuration. For example, the sensor body may employ a living hinge in order to allow promote the movement of the first portion and the second portion relative to one another as the sensor moves between the closed position and the open position. Further, in certain embodiments (not shown), it may be advantageous for the sensor body to form a sleeve-like structure into which a digit may be inserted. Such a configuration may prevent light from leaking into the sides of a sensor.

A flat spring, torsional spring, clip, or other biasing component (e.g. flat spring 12, 30, 40, 51, or 60) as described herein may be constructed from a variety of materials or combinations of materials that provide the desired resiliency and clamping force. For example, in certain embodiments, a flat spring is constructed from stainless steel. In other embodiments, the flat spring 32 is constructed from polymeric materials, such as plastics.

In certain embodiments, it is contemplated that the clip or other closing mechanism has sufficient pressure so that it exceeds the typical venous pressure of a patient, but does not exceed the diastolic arterial pressure. A sensor that applies a pressure greater than the venous pressure will squeeze excess venous blood from the optically probed tissue, thus enhancing the sensitivity of the sensor to variations in the arterial blood signal. Since the pressure applied by the sensor is designed to be less than the arterial pressure, the application of pressure to the tissue does not interfere with the arterial pulse signal. Typical venous pressure, diastolic arterial pressure and systolic arterial pressure are less than 10-35 mmHg, 80 mmHg, and 120 mmHg, respectively. In certain embodiments, the sensor may be adjusted to overcome an average pressure of 15-30 mmHg. These pressures may vary because of the location of the vascular bed and the patient's condition. In other embodiments, low arterial diastolic blood pressure (about 30 mmHg) may occur in sick patients. In such embodiments, the sensor may remove most of the venous pooling with light to moderate pressure (to overcome about 15 mmHg). It is contemplated that removing venous blood contribution without arterial blood exsanguination may improve the arterial pulse signal.

Although the exemplary sensors described herein have depicted a generally U-shaped flat spring, it should be understood that a sliding clip may be a spring or any other biasing mechanism. Further, the clip may be any suitable size or shape appropriate for closing a sensor body around a patient's tissue.

In certain embodiments, it may be advantageous to use a single sliding clip configured to be used in conjunction with a variety of different sensor bodies. For example, a detachable sliding clip, such as a flat spring, may detached from a sensor body adapted to be applied to a patient's digit, and may be then used with a sensor body adapted to be applied to a patient's earlobe. For example, in certain embodiments, pulse oximetry sensor kits may include several sensor bodies, each adapted for a different tissue or digit, and a singe sliding clip that is suitably sized and shaped to be used with each of the sensor bodies.

In an alternate embodiment, it may be advantageous to use a single sensor body with a variety of clips of different sizes. For example, a single sensor body may be arranged to fit on a patient's finger and may be clipped with a first clip. The same sensor body may then be used on a larger patient's finger with a second, larger clip that accommodates the larger tissue. The clips may be selected to be of multiple sizes and/or strengths to provide suitable closing bias and securing strength. For example, a sensor body may be provided with a first clip configured to overcome a normal venous pressure of 15-30 mmHg. The sensor body may also be provided with a second clip that is more appropriate for use with very sick patients that exhibit overall lower blood pressures. The second clip may be configured to overcome lower venous pressures of less than 15 mmHg. In certain embodiments, pulse oximetry sensor kits may include several clips, each adapted for a different tissue or digit, and a singe sensor body that is suitably sized and shaped to be used with each of the various clips.

Keeping in mind the preceding points, the exemplary sensor designs herein are provided as examples of sensors that provide a conformable and secure fit over a variety of patient physiologies. It should be appreciated that a sensor 10 according to the present teachings may be adapted for use on any digit, and may also be adapted for use on a nose bridge, foot, earlobe, or other sensor site.

A sensor, illustrated generically as a sensor 10, may be used in conjunction with a pulse oximetry monitor 68, as illustrated in FIG. 7. It should be appreciated that the cable 70 of the sensor 10 may be coupled to the monitor 68 or it may be coupled to a transmission device (not shown) to facilitate wireless transmission between the sensor 10 and the monitor 68. The monitor 68 may be any suitable pulse oximeter, such as those available from Nellcor Puritan Bennett Inc. Furthermore, to upgrade conventional pulse oximetry provided by the monitor 68 to provide additional functions, the monitor 68 may be coupled to a multi-parameter patient monitor 72 via a cable 74 connected to a sensor input port or via a cable 76 connected to a digital communication port.

The sensor 10 includes an emitter 78 and a detector 80 that may be of any suitable type. For example, the emitter 78 may be one or more light emitting diodes adapted to transmit one or more wavelengths of light in the red to infrared range, and the detector 80 may be a photodetector selected to receive light in the range or ranges emitted from the emitter 78.

The emitter 78 and the detector 80 may be disposed on a sensor body 82, which may be made of any suitable material, such as plastic, rubber, silicone, foam, woven material, or combination thereof. Alternatively, the emitter 78 and the detector 80 may be remotely located and optically coupled to the sensor 10 using optical fibers. In the depicted embodiments, the sensor 10 is coupled to a cable 70 that is responsible for transmitting electrical and/or optical signals to and from the emitter 78 and detector 80 of the sensor 10. The cable 70 may be permanently coupled to the sensor 10, or it may be removably coupled to the sensor 10—the latter alternative being more useful and cost efficient in situations where the sensor 10 is disposable.

The sensor 10 may be a "transmission type" sensor. Transmission type sensors include an emitter 78 and detector 80 that are typically placed on opposing sides of the sensor site. If the sensor site is a fingertip, for example, the sensor 10 is positioned over the patient's fingertip such that the emitter 78 and detector 80 lie on either side of the patient's nail bed. In other words, the sensor 10 is positioned so that the emitter 78 is located on the patient's fingernail and the detector 80 is located 180° opposite the emitter 78 on the patient's finger pad. During operation, the emitter 78 shines one or more wavelengths of light through the patient's fingertip and the light received by the detector 80 is processed to determine various physiological characteristics of the patient. In each of the embodiments discussed herein, it should be understood that the locations of the emitter 78 and the detector 80 may be exchanged. For example, the detector 80 may be located at the top of the finger and the emitter 78 may be located underneath the finger. In either arrangement, the sensor 10 will perform in substantially the same manner.

For pulse oximetry applications using either transmission or reflectance type sensors the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

Although the embodiments described herein generally referred to transmission type sensors, it should be understood that the sensor 10 may be a reflectance type sensor. Reflectance type sensors generally operate under the same general principles as transmittance type sensors. However, reflectance type sensors include an emitter 78 and detector 80 that are typically placed on the same side of the sensor site. For example, a reflectance type sensor may be placed on a patient's fingertip or forehead such that the emitter 78 and detector 80 lie side-by-side. Reflectance type sensors detect light photons that are scattered back to the detector 80.

While the pulse oximetry sensor 10 discussed herein is one example of an exemplary medical device, other such devices are also contemplated and fall within the scope of the present disclosure. For example, other medical sensors and/or contacts applied externally to a patient may be advantageously applied using a clip-style sensor body as discussed herein. Examples of such sensors or contacts may include glucose monitors or other sensors or contacts which are generally held adjacent to the skin of a patient such that a conformable and comfortable fit is desired.

While the invention may be susceptible to various modifications and alternative forms, specific embodiments have been shown by way of example in the drawings and have been described in detail herein. However, it should be understood that the invention is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, intravascular dyes, and/or water content. The invention is to cover all modifications, equivalents, and alternatives falling within the spirit and scope of the invention as defined by the following appended claims.

What is claimed is:

1. A sensor, comprising:
 a sensor body comprising a first portion and a second portion, wherein at least one of the first portion and the second portion comprises an alignment feature;
 at least one sensing element disposed on the sensor body; and
 a sliding clip adapted to slide along the sensor body to bias the first portion towards the second portion, wherein the sliding clip is adapted to apply a pressure to a patient's tissue sufficient to overcome the patient's venous blood pressure but not sufficient to overcome the patient's arterial blood pressure, and wherein the sliding clip is generally U-shaped and configured to be disposed along the alignment feature.

2. The sensor, as set forth in claim 1, wherein the sliding clip comprises a flat spring.

3. The sensor, as set forth in claim 1, wherein the sensor body comprises a restraining clip adapted to hold the sliding clip on the sensor body.

4. The sensor, as set forth in claim 3, wherein the sliding clip comprises a guard adapted to collide with the restraining clip to block the sliding clip from being detached from the sensor body.

5. The sensor, as set forth in claim 1, wherein the applied pressure is between about 10 mm Hg and about 80 mm Hg.

6. The sensor, as set forth in claim 1, wherein the applied pressure is between about 10 mm Hg and about 35 mm Hg.

7. A sensor, comprising:
 a sensor body comprising a first portion and a second portion, wherein at least one of the first portion and the second portion comprises an alignment feature;
 at least one sensing element disposed on the sensor body; and
 a sliding clip adapted to move between an engaged position and a disengaged position, wherein the first portion and the second portion are biased towards one another when the sliding mechanism is in the engaged position, wherein the sliding clip is adapted to apply a pressure to a patient's tissue sufficient to overcome the patient's venous blood pressure but not sufficient to overcome the patient's arterial blood pressure, and wherein the sliding clip is generally U-shaped and configured to be disposed along the alignment feature.

8. The sensor, as set forth in claim 7, wherein the sensor comprises at least one of a pulse oximetry sensor or a sensor for measuring a water fraction.

9. A pulse oximetry system, comprising:
 a pulse oximeter monitor; and
 a pulse oximetry sensor configured to communicate with the pulse oximetry monitor, the pulse oximetry sensor comprising:
  a sensor body comprising a first portion and a second portion, wherein at least one of the first portion and the second portion comprises an alignment feature;

at least one sensing element disposed on the sensor body; and a sliding clip adapted to slide along the sensor body to bias the first portion towards the second portion, wherein the sliding clip is adapted to apply a pressure to a patient's tissue sufficient to overcome the patient's venous blood pressure but not sufficient to overcome the patient's arterial blood pressure, and wherein the sliding clip is generally U-shaped and configured to be disposed along the alignment feature.

10. The pulse oximetry system, as set forth in claim 9, wherein the sensing element comprises an emitter and a detector.

11. A method of manufacturing a sensor kit, comprising:
providing a sensor body comprising a first portion and a second portion and having at least one sensing element disposed thereon; and
providing a plurality of sliding clips adapted to slide along the sensor body to bias the first portion towards the second portion, wherein each sliding clip of the plurality of sliding clips is adapted to apply a different pressure to a patient's tissue such that at least one of the clips applies a pressure sufficient to overcome the patient's venous blood pressure but not sufficient to overcome the patient's arterial blood pressure.

12. The method, as set forth in claim 11, comprising:
providing a retaining element configured to attach each sliding clip of the plurality of sliding clips to the sensor body.

13. A method of applying a sensor, comprising:
inserting a patient's tissue into a sensor body comprising at least one sensing element; and
after the inserting, sliding a clip into an engaged position, wherein the sliding clip is adapted to apply a pressure to a patient's tissue sufficient to overcome the patient's venous blood pressure but not sufficient to overcome the patient's arterial blood pressure, and wherein the sliding clip is generally U-shaped.

14. The method, as set forth in claim 13, comprising:
embedding the clip in the sensor body.

15. A pulse oximetry sensor kit, comprising:
a first sensor body having a first size adapted for use on a first tissue site, the first sensor body comprising:
a first portion and a second portion; and
at least one sensing element disposed on the first sensor body;
a second sensor body having a second size different than the first size and adapted for use on a second tissue site different than the first tissue site, the second sensor body comprising:
a first portion and a second portion; and
at least one sensing element disposed on the second sensor body; and
at least one detachable clip, wherein the detachable clip is adapted to slide along the first sensor body and the second sensor body.

16. The kit, as set forth in claim 15, wherein the first tissue site and the second tissue site comprise a different one of a digit, nose bridge, foot, or ear lobe.

17. A pulse oximetry sensor kit, comprising:
at least one sensor body comprising:
a first portion and a second portion;
at least one sensing element disposed on the sensor body;
a first detachable clip having a first size adapted to bias the first portion towards the second portion with a first pressure; and a second detachable clip having a second size different than the first size adapted to bias the first portion towards the second portion with a second pressure different than the first pressure.

18. A sensor, comprising:
a sensor body comprising a first portion and a second portion, wherein the first portion and the second portion comprise a first passage and a second passage, respectively;
at least one sensing element disposed on the sensor body; and
a detachable clip adapted to bias the first portion towards the second portion when the detachable clip is inserted in the first passage and the second passage, wherein the detachable clip is at least partially embedded in the sensor body when inserted in the first passage and the second passage, and wherein the detachable clip is generally U-shaped.

19. The sensor, as set forth in claim 18, wherein the detachable clip comprises a handle.

20. The sensor, as set forth in claim 18, wherein the sensor body comprises an overmolded internal framework.

21. A pulse oximetry system, comprising:
a pulse oximeter monitor; and
a pulse oximetry sensor configured to communicate with the pulse oximetry monitor, the pulse oximetry sensor comprising:
a sensor body comprising a first portion and a second portion, wherein the first portion and the second portion comprise a first passage and a second passage, respectively;
at least one sensing element disposed on the sensor body; and
a detachable clip adapted to bias the first portion towards the second portion when the detachable clip is inserted in the first passage and the second passage, wherein the detachable clip is at least partially embedded in the sensor body when inserted in the first passage and the second passage, and wherein the detachable clip is generally U-shaped.

22. The pulse oximetry system, as set forth in claim 21, wherein the sensing element comprises an emitter and a detector.

23. A method of manufacturing a sensor kit, comprising:
providing a sensor body comprising a first portion and a second portion, wherein the first portion and the second portion comprise a first passage and a second passage, respectively, and having at least one sensing element disposed thereon; and
providing a plurality of detachable clips adapted to bias the first portion towards the second portion when each detachable clip of the plurality of detachable clips is inserted in the first passage and the second passage, wherein each detachable clip of the plurality of detachable clips is at least partially embedded in the sensor body when inserted in the first passage and the second passage.

24. The method, as set forth in claim 23, comprising:
providing a depression in the sensor body.

25. A method of applying a sensor, comprising:
inserting a patient's tissue into a sensor body having a first portion and a second portion and at least one sensing element; and
embedding a first end and a second end of a detachable clip in the sensor body to bias the first portion towards the second portion.

* * * * *